US005837734A

United States Patent [19]
Bartsch et al.

[11] Patent Number: 5,837,734
[45] Date of Patent: Nov. 17, 1998

[54] METHOD FOR THE TREATMENT OF COCCIDIOIDOMYCOSIS IN WARM-BLOODED ANIMALS

[75] Inventors: Robert C. Bartsch; Russell T. Greene, both of Phoenix, Ariz.

[73] Assignee: Novartis Corporation, Summit, N.J.

[21] Appl. No.: 640,606

[22] Filed: May 1, 1996

[51] Int. Cl.$^6$ .......... A61K 31/17

[52] U.S. Cl. .......... 514/594

[58] Field of Search .......... 514/594

[56] References Cited

U.S. PATENT DOCUMENTS 5,420,163 5/1995 Potter et al. .......... 514/594

OTHER PUBLICATIONS

Textbook of Veterinary Internal Medicine, Fourth Edition, vol. 1, Chapter 71, Deep Myrotic Diseases, Wolf et al. pp. 443–448 (1995).

New Horizons in Microbiology, "Pre–Clinical Evaluation of Antifungal Drugs for Deep Mucosis"(1984) pp. 317–323.

Clinical Infectious Diseases, vol. 14, No. 1, 1992, Galgiani, pp. s100–s105.

*Primary Examiner*—Jerome Goldberg
*Attorney, Agent, or Firm*—William A. Teoli, Jr.

[57] ABSTRACT

This invention relates to the use of acyl urea compounds for the treatment or prophylaxis of *Coccidioides immitis* infections in warm-blooded animals. The invention has particular application in the treatment, prophylaxis or reduction of coccidioidomycosis.

20 Claims, No Drawings

METHOD FOR THE TREATMENT OF COCCIDIOIDOMYCOSIS IN WARM-BLOODED ANIMALS

TECHNICAL FIELD

This invention relates to the use of acyl urea compounds for the treatment or prophylaxis of *Coccidioides immitis* infections in warm-blooded animals. The invention has particular application in the treatment, prophylaxis or reduction of coccidioidomycosis.

BACKGROUND

Acyl ureas, including processes for their preparation, are known in the art and are described, for example, in U.S. Pat. No, 5,420,163. The class of acyl urea compounds disclosed in U.S. Pat. No. 5,420,163 is described as parasitidal. Endoparasites and ectoparasites such as fleas, mange mites and helminths are among the illustrative parasites. There is no reference to activity against fungi such as *Coccidioides immitis* or diseases such as coccidioidomycosis.

*Coccidioides immitis* (*C. immitis*) is a geophilic, dimorphic fungus that is endemic to the southwestern United States, including parts of California, Nevada, Utah, Arizona, New Mexico, and Texas. *C. immitis* is also widespread in parts of Mexico and in Central and South America. Active growth of the free-living mycelial phase of *C. immitis* in the soil follows winter rains and produces arthroconidia. Infection of warm-blooded animals is most likely to occur in the summer months when hot, dry conditions favor inhalation of *C. immitis* arthroconidia spread by wind or by physical disturbance of infected soil.

Once inside the warm-blooded animal host, the *C. immitis* arthroconidia are transformed to the parasitic spherular phase. These large spherules (20 to 100 $\mu$m) grow, mature, and divide internally to produce endospores. When released, the endospores spread the *C. immitis* infection locally or to distant sites via lymphatics or blood.

Acute, primary pulmonary coccidioidomycosis usually occurs within one to three weeks following *C. immitis* infection. Early clinical signs may be absent or include a mild nonproductive cough, low-grade fever, partial anorexia, and weight loss. This form of disease is often self-limiting but may progress to disseminated infection. Disseminated pulmonary coccidioidomycosis causes a more severe productive cough due to widespread lung involvement and tracheobronchial lymphadenopathy. Systemic signs include an antibiotic-unresponsive fluctuating fever, depression, weakness, anorexia, and weight loss. As noted above, *C. immitis* may spread beyond the pulmonary tree to affect any organ or system in the body via lymphatics or blood.

The mean age of incidence for coccidioidomycosis in dogs, for example, has been reported as 1.5 to 4.0 years; males are more likely to be affected. Sporting dogs (hounds), Boxers, and Doberman pinschers may be particularly susceptible to developing coccidioidomycosis.

Currently available treatments for coccidioidomycosis in warm-blooded animals include systemic antifungal chemotherapy. For example, the imidazoles such as ketoconazole and itraconazole are used for the treatment of coccidioidomycosis in the dog and cat. In addition, liposome-encapsulated amphotericin B has been shown to be safe and effective in the treatment of coccidioidomycosis in those dogs that cannot tolerate oral imidazole therapy. However, *C.immitis* is more resistant to amphotericin B than the other systemic mycotic agents.

In view of the problems of patient tolerance and drug resistance which arise from time to time during currently available treatments, there continues to be a need for new chemotheraputic agents and methods for treating *C.immitis* infections in warm-blooded animals and related diseases implicated by such infections including coccidioidomycosis.

SUMMARY

It has now been found, surprisingly, that certain compounds of the acyl urea class are useful for the treatment or prophylaxis of *Coccidioides immitis* infections in warm-blooded animals, as well as the treatment, prophylaxis, or reduction of conditions, diseases or syndromes implicated by such infections.

The method of the invention comprises administering to a warm-blooded animal in need of the treatment or prophylaxis of a *C.immitis* infection an antifungal effective amount of a compound represented by the formula:

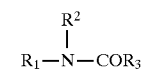

(I)

wherein $R_1$, $R_2$ and $R_3$ are as defined hereinafter.

DETAILED DESCRIPTION

As indicated above, the present invention relates to a method for the treatment or prophylaxis of *C.immitis* infections in warm-blooded animals.

Acyl urea compounds suitable for use in the method of the present invention include the following compounds of formula I 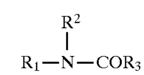 (I)

wherein $R_1$ is unsubstituted or substituted phenyl, naphthyl, pyridyl, pyridazinyl, pyrimidinyl or pyrazinyl, $R_2$ is hydrogen or $C_1$–$C_6$alkyl, $R_3$is 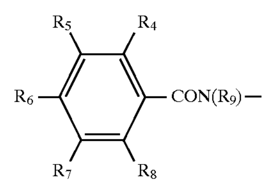 or 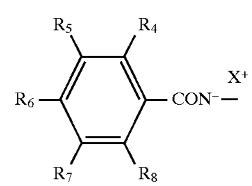 $R_4$ to $R_8$ are each independently hydrogen, halogen, $C_1$–$C_6$-alkyl, $C_1$–$C_6$haloalkyl, $C_1$–$C_6$alkoxy, $C_1$–$C_6$-haloalkoxy or $C_1$–$C_6$alkylthio, $R_9$ is hydrogen or $C_1$–$C_6$alkyl, and $X^+$ is a pharmaceutically or agronomically acceptable inorganic or organic cation.

In the compounds of formula (I), suitable inorganic cations ($X^+$) are, for example, alkali metal and alkaline earth metal cations; and suitable organic cations (X⁺) are, for example, characterized by the group

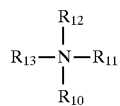

or

in which formulae, $R_{10}$ to $R_{13}$ are each independently hydrogen, $C_1$–$C_{20}$alkyl, benzyl, or phenyl and $R_{14}$ is hydrogen or $C_1$–$C_{20}$alkyl e.g. H₄N+, (CH₃)₄N+, (C₂H₅)₄N+, (n-C₃H₇)₄N+, (i-C₃H₇)₄N+, (n-C₄H₉)₄N+,

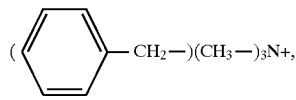

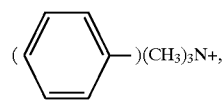

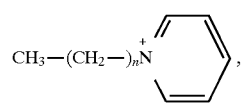

or

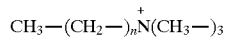

n being a value from 8 to 15.

Other pharmaceutically or agronomically acceptable salts of the acyl ureas of formula (I) also are contemplated.

For example, those compounds of formula (I) which have a basic centre can form acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$-)alkanecarboxylic acids which, for example, are unsubstituted or substituted by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, benzoic acid or with organic sulfonic acids, such as ($C_1$–$C_4$-)alkane- or arylsulfonic acids which are unsubstituted or substituted, for example, by halogen, for example methane- or toluenesulfonic acid.

Particularly preferred compounds for use in the present method are the benzoylurea compounds represented by the formula:

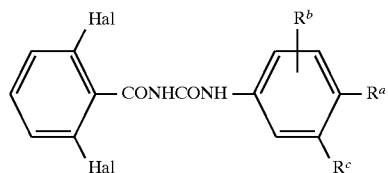

wherein:

Hal is independently chloro; bromo; or fluoro.

$R^a$ is hydrogen; chloro; bromo; fluoro; methyl; trifluoromethyl;

trifluoromethoxy; 2-chloro-1,1,2-trifluoroethoxy; 2-bromo-1,1,2-triflouroethoxy; 1,1,2,2-tetrafluoroethoxy; or 1,1,2,3,3,3-hexafluoroprop-1-oxy;

$R^b$ is hydrogen or chloro; and $R^c$ is hydrogen; chloro; 5-trifluoromethylpyrid-2-yloxy; or 3-chloro-5-trifluoromethylpyrid-2-yloxy;

at least one of $R^a$ and $R^c$ being other than hydrogen; and pharmaceutically or agronomically aceptable salts thereof.

Preferred subgroups are those in which Hal is fluoro, and one of $R^a$ and $R^b$ is an ether group. Thus a first preferred subgroup are benzoylureas of Formula II in which $R^a$ is hydrogen, methyl, or chloro;

$R^b$ is hydrogen; and $R^c$ is 5-trifluoromethylpyrid-2-yloxy or 3-chloro-5-trifluoromethylpyrid-2-yloxy.

A second preferred subgroup are benzoylureas of Formula II in which $R^a$ is 2-chloro-1,1,2-trifuoromethoxy, 2-bromo-1,1,2-trifluoromethoxy; 1,1,2,2-tetrafluoroethoxy; or 1,1,2,3,3,3-hexafluoroprop-1-oxy; $R^b$ is chloro; and $R^c$ is chloro, that is an N-(2,6-difluorobenzoyl)-N'-(3,6-dichloro-4-$R^a$-phenyl)urea or N-(2,6-difluorobenzoyl)-N'-(3,5-dichloro-4-$R^a$-phenyl)urea.

Representative examples of particularly preferred individual compounds are:

N-(2,6-difluorobenzoyl)-N'-[3-(3-chloro-5-trifluoromethylpyri d-2-yloxy)-4-bromophenyl]urea, N-(2,6-difluorobenzoyl)-N'-[3-(3-chloro-5-trifluoromethylpyrid-2-yloxy)-4-methylphenyl]urea, N-(2,6-difluorobenzoyl)-N'-[3-(3-chloro-5-trifluoromethyl-pyrid-2-yloxy)-4-chlorophenyl]urea, N-(2,6-difluorobenzoyl)-N'-[3-(3-chloro-5-trifluoromethylpyrid-2-yloxy)-4-fluorophenyl]urea, N-(2,6-difluorobenzoyl)-N'-[3-(5-trifluoromethylpyrid-2-yloxy)-4-bro mophenyl]urea, N-(2,6-difluorobenzoyl)-N'-[3-(5-trifluoromethylpyrid-2-yloxy)-4-methylphenyl]urea, N-(2,6-difluorobenzoyl)-N'-[3-(5-trifluoromethylpyrid-2-yloxy)-4-chlorophenyl]urea, N-(2,6-difluorobenzoyl)-N'-[3-(5-trifluoromethylpyrid-2-yloxy)-4-fluorophenyl]urea, N-(2,6-difluorobenzoyl)-N'-[3,5-dichloro-4-(2-chloro-1,1,2-trifluoroethoxy)phenyl]urea, N-(2,6-difluorobenzoyl)-N'-[3,6-dichloro-4-(2-chloro-1,1,2-trifluoroethoxy)phenyl]urea, N-(2,6-difluorobenzoyl)-N'-[3,5-dichloro-4-(1,1,2,3,3,3-hexafluoroprop-2-oxy)phenyl]urea, N-(2,6-difluorobenzoyl)-N'-[3,6-dichloro-4-(1,1,2,3,3,3-hexafluoroprop-1-oxy)phenyl]urea, N-(2,6-difluorobenzoyl)-N'-[3,5-dichloro-4-(2-bromo-1,1,2-trifluoroethoxy)phenyl]urea, N-(2,6-difluorobenzoyl)-N'-[3,6-dichloro-4-(2-bromo-1,1,2-trifluoroethoxy)phenyl]urea, N-(2,6-difluorobenzoyl)-N'-[3,5-dichloro-4-(1,1,2,2-tetrafluoroethoxy)phenyl]urea, and N-(2,6-difluorobenzoyl)-N'-[3,6-dichloro-4-(1,1,2,2-tetrafluoroethox y)pheny]urea.

In accordance with the present invention, administration of at least one acyl urea compound to the warm-blooded animal host is achieved with several forms of application, e.g. by administering a formulated active ingredient orally. In this case, the term "formulated" means in the form of a powder, a tablet, a granulate, capsule, an emulsion, a foam, etc. The preparation does not necessarily have to be administered to the animal direct; it may be convenient to mix it with the animal's feed.

The method of the present invention also contemplates the treatment or prophylaxis of *C.immitis* infections in warm-blooded animals by administration of at least one acyl urea in conjunction with one or more known antifungal or mycotic agents. Suitable mixing partners include the imidazoles such as ketoconazole and itraconazole as well as the compound amphotericin B.

Representative warm-blooded animal hosts which may be treated in accordance with the method of the present invention include humans and domestic animals such as cattle, horses, sheep, goats, poultry, swine, dogs, cats and zoo animals.

The time, manner, and rates at which the acyl urea compounds of formulae (I) or (II) are effectively administered for the prophylaxis or treatment of *C. immitis* infections in a host warm-blooded animal may be varied over a wide range. Therapeutically effective amounts of the acyl urea compounds can be administered to the host animals at rates from about 0.01 to about 1000 mg/kg of animal body weight. The best rate for a given animal must be determined individually, but it is generally found that in most cases the optimum rate is within the range of from about 0.25 to about 100 mg/kg of host animal body weight. The optimum rate for a given instance depends, for example, on such factors as the activity of the specific acyl urea compound or compounds, the level of *C. immitis* infection, whether a prophylactic regimen in being followed, the method of administration, and the health of the host animal being treated. Doses are usefully regularly repeated at daily, weekly, biweekly and monthly intervals. The most suitable interval for administration must be determined on a case-by-case basis.

For treatment of a specific disease such as coccidioidomycosis, it is generally found that the optimum dosage rate of acyl ureas (I) or (II) is within the range of from about 1 to about 20 mg per kg of host animal body weight per day, more particularly, from about 2.5 to about 12 mg/kg per day. The treatment may continue for a period of several weeks or months depending upon the severity of the clinical symptoms.

In one embodiment, the acyl ureas of formulae (I) or (II) are conveniently applied in a dose of about 0.01 to 800, preferably about 0.5 to 200, more preferably 1 to 30, most preferably 2.5 to 12 mg/kg body weight, based on the host animal, with oral administration being preferred. A good dose for regular administration is in general in the range from 1 to 100 mg/kg body weight of the host animal.

The total dose of the acyl ureas of formulae (I) and (II) can vary from one genus of animal to the other and can even vary within the same genus since said dose depends, inter alia, on the weight and constitution of the animal, the degree or severity of the *C. immitis* infection and on the seasonal period for prophylaxis of *C. immitis*.

In accordance with the method of the invention, the prophylaxis or treatment of *C. immitis* infections in a host warm-blooded animal is achieved by orally, percutaneously or otherwise parenterally administering at least one acyl urea compound of formula (I) to such host warm-blooded animal. Administration by way of a suppository also is contemplated.

Oral application can be in the form of tablets, capsules, lick-stones, bolus, drinking water, or granules. Parenteral administration can be accomplished by means of injection, implantation, or transdermal application.

In addition to containing adjuvants conventionally employed in the art of formulation, the compositions to be administered orally may of course contain further additives which stimulate voluntary ingestion by the animal, e.g. suitable scents or flavorings.

Owing to its simplicity, oral application is one of the preferred objects of the present invention. A further mode of application is parenteral application, e.g. by subcutaneous, intravenous or intramuscular injection or by means of a sustained action preparation in the form of an implant or other depot formulation.

Methods of oral application include but are not limited to compounds premixed in dog and cat food, fed in biscuits or treats, chewable tablets, water-dissolvable capsules or tablets, water-soluble compounds applied with a dropper into water or materials applied in any form onto dog food. Implants include any device applied into the animal for release of acyl urea compounds to control *Coccidioides immitis* infections.

Percutaneous administration is conveniently accomplished by subcutaneous, dermal, intramuscular and even intravenous application of the injectable formulation. Conventional needle-type injection devices as well as needle-less air-blast injection devices can be used.

It is possible to delay or sustain the permeation of the active ingredient through the animal's living tissues by proper formulation. For example, very insoluble compound may be used. In this case, the slight solubility of the compound causes sustained action because the body fluids of the animal can dissolve only a small amount of the compound at any one time. Sustained action of the active ingredient can also be obtained by formulating the compound in a matrix which will physically inhibit dissolution. The formulated matrix is injected into the body where it remains as a depot from which the compound slowly dissolves.

Matrix formulations, now known in the art, are formulated in waxy semisolids such as vegetable waxes and high molecular weight polyethylene glycols. Very effective sustained action is obtained by introducing into the animal or implant containing one of the active ingredients. Such implants are now well known in veterinary art and are usually made of a silicone-containing rubber. The active ingredient is dispersed through a solid rubber implant or is contained inside a hollow implant. Care must be taken to choose an active ingredient which is soluble in the rubber form which the implant is made, since it is dispersed by first dissolving in the rubber and then leaching out of the rubber into the body fluids of the treated animal.

The rate at which active ingredient is released from an implant, and hence the length of time during which the implant remains effective, is controlled with good accuracy by the proper adjustment of the concentration of the compound in the implant, the external area of the implant, and the formulation of the polymer from which the implant is made.

Administration of the active ingredient by means of an implant is a further particularly useful embodiment. Such administration is highly economical and efficacious because a properly designed implant maintains a constant concentration of the compound in the tissues of the host animal. An implant can be designed to supply compound for several months and is easily inserted in the animal. No further handling of the animal or concern over the dosage is necessary after the insertion of the implant.

The formulation of veterinary additives in animal feed is an extremely well-known art. It is usual to formulate the compound first as a premix in which the active ingredient is dispersed in a liquid or particulate solid carrier. The premix may conveniently contain from about 1 to 800 g of compound per kilogram, depending on the desired concentration in the feed. As is known in the art, many active -ingredients can be hydrolyzed or degraded by constituents of animal feed. Such compounds are routinely formulated in protective matrices such as gelatin before addition to the premix.

In the method of the present invention, the acyl urea normally is not applied in pure form, but preferably in the form of a composition which, in addition to containing the active ingredient, contains application promoters which are tolerated by the host animal.

However, these additional measures are not absolutely necessary. The composition to be applied in the method of this invention usually contains 0.1 to 99% by weight, preferably 0.1 to 95% by weight, of the benzoylurea, and 99.9 to 1% by weight, preferably 0.1 to 25% by weight, of a solid or liquid non-toxic adjuvant, including 0 to 25% by weight, preferably 0.1 to 25% by weight, of a nontoxic surfactant.

Whereas commercial products are preferably formulated as concentrates, the end user will normally employ dilute formulations.

The compositions may also contain further ingredients, such as stabilizers, antifoams, viscosity regulators, binders, tackifiers as well as other active ingredients for obtaining special effects.

Materials known from veterinary practice as being suitable for being administered orally, parenterally or by implant may be employed as formulation assistants. A number of examples are cited below.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragee cores can be provided with suitable coatings that may be resistant to gastric juices, e.g. concentrated sugar solutions which may contain gum arabic, talc, polyvinylpyrrolidone, polyethylene glycol and/or titanium dioxide, or lacquer in suitable organic solvents or solvent mixtures or, for the production of coatings that are resistant to gastric juices, solutions of suitable cellulose preparations, such as acetylcellulose phthalate or hydroxypropylmethylcellulose phthalate. Colorings, flavorings or pigments can be added to the tablets or dragee coatings, for example, for identification purposes or to indicate different dose of active ingredients.

Further orally administrable preparations are dry-filled capsules consisting of gelatine and also soft, sealed capsules consisting of gelatine and a plasticizer, such as glycerol or sorbitol. The dry-filled capsules may contain the active ingredient in the form of a granulate, for example in admixture with fillers, such as lactose, binders, such as starches, and/or glidants, such as talc or magnesium stearate, and optionally stabilizers. In soft capsules, the active ingredient is preferably dissolved or suspended in suitable liquids, such as fatty oils, paraffin oil or liquid polyethylene glycols, it being possible also to add stabilizers. Preferred are, inter alia, capsules that can be easily bitten through or swallowed without being chewed.

Especially suitable for parenteral administration are aqueous solutions of an active ingredient in water-soluble form, for example a water-soluble salt, also suspensions of the active ingredient, sch as corresponding oily injection suspensions, e.g. suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran, and, optionally, also stabilizers.

The preparations of the present invention can be manufactured in a manner known per se, for example by means of conventional mixing, granulating, confectioning, dissolving or lyophilizing processes. For example, pharmaceutical preparations for oral administration can be obtained by combining the active ingredient with solid carriers, optionally granulating a resultant mixture, and processing the mixture or granulate, if desired or necessary after the addition of suitable adjuncts, to form tablets or dragee cores.

The following Examples illustrate the invention described hereinbefore, but do not limit its scope in any way. In these examples, the active ingredient can include any of:

N-(2,6-difluorobenzoyl)-N'-[3-(3-chloro-5-trifluoromethylpyrid-2-yloxy)-4-bromophenyl]urea, N-(2,6-difluorobenzoyl)-N'-[3-(3-chloro-5-trifluoromethylpyrid-2-yloxy)-4-methylphenyl]urea, N-(2,6-difluorobenzoyl)-N'-[3-(3-chloro-5-trifluoromethyl-pyrid-2-yloxy)-4-chlorophenyl]urea, N-(2,6-difluorobenzoyl)-N'-[3-(3-chloro-5-trifluoromethylpyrid-2-yloxy)-4-fluorophenyl]urea, N-(2,6-difluorobenzoyl)-N'-[3-(5-trifluoromethylpyrid-2-yloxy)-4-bro mophenyl]urea, N-(2,6-difluorobenzoyl)-N'-[3-(5-trifluoromethylpyrid-2-yloxy)-4-methylphenyl]urea, N-(2,6-difluorobenzoyl)-N'-[3-(5-trifluoromethylpyrid-2-yloxy)-4-chlorophenyl]urea, N-(2,6-difluorobenzoyl)-N'-[3-(5-trifluoromethylpyrid-2-yloxy)-4-fluorophenyl]urea, N-(2,6-difluorobenzoyl)-N'-[3,5-dichloro-4-(2-chloro-1,1,2-trifluoroethoxy)phenyl]urea, N-(2,6-difluorobenzoyl)-N'-[3,6-dichloro-4-(2-chloro-1,1,2-trifluoroethoxy)phenyl]urea, N-(2,6-difluorobenzoyl)-N'-[3,5-dichloro-4-(1,1,2,3,3,3-hexafluoroprop-2-oxy)phenyl]urea, N-(2,6-difluorobenzoyl)-N'-[3,6-dichloro-4-(1,1,2,3,3,3-hexafluoroprop-1-oxy)phenyl]urea, N-(2,6-difluorobenzoyl)-N'-[3,5-dichloro-4-(2-bromo-1,1,2-trifluoroethoxy)phenyl]urea, N-(2,6-difluorobenzoyl)-N'-[3,6-dichloro-4-(2-bromo-1,1,2-trifluoroethoxy)phenyl]urea, N-(2,6-difluorobenzoyl)-N'-[3,5-dichloro-4-(1,1,2,2-tetrafluoroethoxy)phenyl]urea, and N-(2,6-difluorobenzoyl)-N'-[3,6-dichloro-4-(1,1,2,2-tetrafluoroethoxy)phenyl]urea.

EXAMPLE 1

Tablets containing 25 mg of active ingredient can be manufactured as follows:

| Constituents (for 1000 tablets) | |
| --- | --- |
| active ingredient | 25.0 g |
| lactose | 100.7 g |
| wheat starch | 7.5 g |
| polyethylene glycol (mol. wt. 6000) | 5.0 g |
| talc | 5.0 g |
| magnesium stearate | 1.8 g |
| demineralized water | q.s |

Manufacture

All the solid ingredients are first forced through a sieve having a mesh width of 0.6 mm. Then the active ingredient, the lactose, the talc, the magnesium stearate and half of the starch are mixed. The other half of the starch is suspended in 40 ml of water and this suspension is added to a boiling solution of the polyethylene glycol in 100 ml of water. The resulting starch paste is added to the main batch and the mixture, if necessary with the addition of water, is granulated. The granulate is dried overnight at 35. degree. C., forced through a sieve having a mesh width of 1.2 mm and pressed to form tablets having a diameter of approximately 6 mm that are concave on both sides.

EXAMPLE 2

Tablets containing 0.02 g of active ingredient are manufactured as follows:

| Composition | |
| --- | --- |
| active ingredient | 200.00 g |
| lactose | 290.80 g |
| potato starch | 24.70 g |
| stearic acid | 10.00 g |
| talc | 200.00 g |
| magnesium stearate | 2.50 g |
| colloidal silica | 32.00 g |
| ethanol | q.s. |

A mixture of the active ingredient, the lactose and 194.70 g of the potato starch is moistened with an ethanolic solution of the stearic acid and granulated through a sieve. After drying, the remainder of the potato starch, the talc, the magnesium, and the colloidal silica are admixed and the mixture is pressed to form 0.1 g tablets which, if desired, can be provided with breaking grooves for finer adjustment of the dosage.

EXAMPLE 3

Capsules containing 0.025 g of the active ingredient can be manufactured as follows:

| Composition (for 1000 capsules) | |
| --- | --- |
| active ingredient | 25.00 g |
| lactose | 249.00 g |
| gelatine | 2.00 g |
| corn starch | 10.00 g |
| talc | 15.00 g |
| water | q.s. |

The active ingredient is mixed with the lactose and the mixture is moistened uniformly with an aqueous solution of the gelatine and granulated through a sieve having a mesh width of 1.2–1.5 mm. The granulate is mixed with dried corn starch and the talc is introduced in portions of 300 mg into hard gelatine capsules (size 1).

EXAMPLE 4

Premix (Feed Additive):

0.25 parts by weight of active ingredient and 4.75 parts of secondary calcium phosphate, or China clay, aerosol or carbonate or line are homogeneously mixed with 95 parts of an animal feed.

EXAMPLE 5

Injection Solution 8 parts by weight active ingredient 3.6 parts of acetic acid 88.4 parts of water for injection The acetic acid and the water are added to the active ingredient and the mixture is stirred until everything has dissolved. The solution is then filtered and sterilized by a suitable method. pH of the solution: 5.0.

EXAMPLE 6

Emulsifiable Concentrate:

20 parts of active ingredient are mixed with 20 parts of emulsifier, e.g. a mixture of alkylarylpolyglycol ether with alkylaryl sulphonates, and 60 parts of solvent until the solution is completely homogeneous.

By diluting this concentrate with water it is possible to obtain an emulsion of the desired concentration.

EXAMPLE 7

Solutions (For Dilution With Drinking Water):

15% active ingredient in 2,2-dimethyl-4-hydroxy methyl1-1,3-dioxolane

10% active ingredient in diethylene glycol monethyl ether

10% active ingredient in polyethylene glycol (mol. wt. 300)

5% active ingredient in glycerol

EXAMPLE 8

Soluble Powder:

25 parts of active ingredient 1 part of sodium lauryl sulfate 3 parts of colloidal silica 71 parts of urea The constituents are mixed and the mixture is finely ground in a suitable mill. Other biocidal active ingredients or agents which are inert towards the active ingredients and acceptable to the animals to be treated, or mineral salts or vitamins can be admixed to the compositions described.

EXAMPLE 9

Composition of the Anti-*C. immtis* Drug

Active ingredient Tablets

| Ingredient | Am $R_3$ is

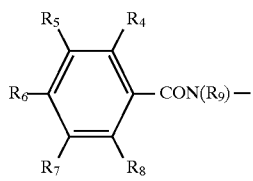

or

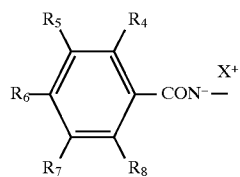

$R_4$ to $R_8$ are each independently hydrogen, halogen, $C_1$–$C_6$-alkyl, $C_1$–$C_6$haloalkyl,
$C_1$–$C_6$alkoxy, $C_1$–$C_6$-haloalkoxy or $C_1$–$C_6$alkylthio,
$R_9$ is hydrogen or $C_1$–$C_6$alkyl, and
$X^+$ is a pharmaceutically or agronomically acceptable inorganic or organic cation; and pharmaceutically or agronomically acceptable salts thereof.

2. The method according to claim 1 in which in said acyl urea is a benzoylurea compound represented by the formula:

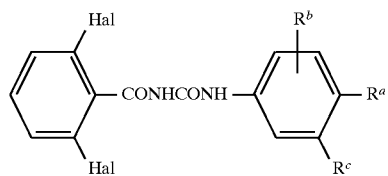

wherein:
Hal is independently chloro; bromo; or fluoro.
$R^a$ is hydrogen; chloro; bromo; fluoro; methyl; trifluoromethyl; trifluoromethoxy; 2-chloro-1,1,2-trifluoroethoxy; 2-bromo- 1,1,2-triflouroethoxy; 1,1,2,2-tetrafluoroethoxy; or 1,1,2,3,3,3-hexafluoroprop-1-oxy;
$R^b$ is hydrogen or chloro; and
$R^c$ is hydrogen; chloro; 5-trifluoromethylpyrid-2-yloxy; or
3-chloro-5-trifluoromethylpyrid-2-yloxy;
at least one of $R^a$ and $R^c$ being other than hydrogen; and pharmaceutically or agronomically acceptable salts thereof.

3. The method according to claim 2 wherein said benzoylurea is
N-(2,6-difluorobenzoyl)-N'-(3,6-dichloro-4-$R^a$-phenyl) urea in which
$R^a$ is 2-chloro-1,1,2-trifluoroethoxy; 2-bromo-1,1,2-trifluoroethoxy;
1,1,2,2-tetrafluoroethoxy; or
1,1,2,3,3,3-hexafluoroprop-1-oxy.

4. The method according to claim 3 wherein said benzoylurea is
N-(2,6-difluorobenzoyl)-N'-(3,5-dichloro-4-$R^a$-phenyl) urea in which
$R^a$ is 2-chloro-1,1,2-trifluoroethoxy;
2-bromo-1,1 ,2-trifluoroethoxy;
1,1,2,2-tetrafluoroethoxy; or 1,1,2,3,3,3-hexafluoroprop-1-oxy.

5. The method according to claim 1 wherein said acyl urea is administered orally, parenterally or through implantation.

6. The method according to claim 5 wherein the amount of said acyl urea administered is from 0.01 to about 1000 mg per kg of body weight.

7. The method according to claim 6 wherein the amount of said acyl urea administered is from 1 to about 30 mg per kg of body weight.

8. The method according to claim 6 wherein the amount of said acyl urea administered is from 0.5 to about 200 mg per kg of body weight.

9. The method according to claim 5 in which said benzoylurea is N-(2,6-difluorobenzoyl)-N'-[3,5-dichloro-4-(2-chloro-1,1,2-trifluoro-1-ethoxy)phenyl]urea.

10. The method according to claim 5 in which said benzoylurea is N-(2,6-difluorobenzoyl)-N'-[3,6-dichloro-4-(2-chloro-1,1,2-trifluoro-1-ethoxy)phenyl]urea.

11. The method according to claim 5 in which said benzoylurea is N-(2,6-difluorobenzoyl)-N'-[3,5-dichloro-4-(1,1,2,3,3,3-hexafluoroprop-1-oxy)-phenyl]urea.

12. The method according to claim 5 in which said benzoylurea is N-(2,6-difluorobenzoyl)-N'-[3,6-dichloro-4-(1,1,2,3,3,3-hexafluoroprop-1-oxy)-phenyl]urea.

13. The method according to claim 5 in which said benzoylurea is N-(2,6-difluorobenzoyl)-N'-[3,5-dichloro-4-(2-bromo-1,1,2-trifluoro-1-ethoxy)phenyl]urea.

14. The method according to claim 5 in which said benzoylurea is N-(2,6-difluorobenzoyl)-N'-[3,6-dichloro-4-(2-bromo-1,1,2-trifluoroethoxy)phenyl]urea.

15. The method according to claim 5 in which said benzoylurea is N-(2,6-difluorobenzoyl)-N'-[3,5-dichloro-4-(1,1,2,2-tetrafluoroethoxy)phenyl]urea.

16. The method according to claim 5 in which said benzoylurea is N-(2,6-difluorobenzoyl)-N'-[3,6-dichloro-4-(1,1,2,2-tetrafluoroethoxy)phenyl]urea.

17. A method for the treatment or prophylaxis of coccidioidomycosis in a host dog or cat comprises administering to a dog or cat in need of such treatment a therapeutic effective amount of an acyl urea represented by the following formula:

wherein $R_1$ is unsubstituted or substituted phenyl, naphthyl, pyridyl, pyridazinyl, pyrimidinyl or pyrazinyl,
$R_2$ is hydrogen or $C_1$–$C_6$alkyl,
$R_3$ is

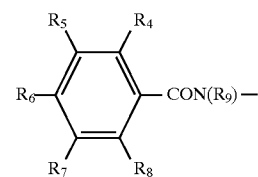

or

-continued

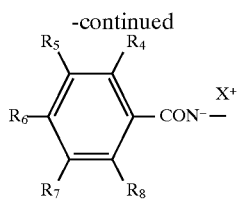

$R_4$ to $R_8$ are each independently hydrogen, halogen, $C_1$–$C_6$-alkyl, $C_1$–$C_6$haloalkyl, $C_1$–$C_6$alkoxy, $C_1$–$C_6$-haloalkoxy or $C_1$–$C_6$alkylthio, $R_9$ is hydrogen or $C_1$–$C_6$alkyl, and $X^+$ is a pharmaceutically or agronomically acceptable inorganic or organic cation; and pharmaceutically or agronomically acceptable salts thereof.

18. The method according to claim 17 wherein said acyl urea is administered orally, parenterally or through implantation.

19. The method according to claim 18 wherein the amount of said acyl urea administered is from 0.01 to about 1000 mg per kg of body weight.

20. The method according to claim 18 in which said acyl urea is N-(2,6-difluorobenzoyl)-N'-[3,6-dichloro-4-(1,1,2,3,3,3-hexafluoroprop-1-oxy)-phenyl]-urea.

* * * * *